United States Patent
Li et al.

(10) Patent No.: US 11,484,202 B2
(45) Date of Patent: Nov. 1, 2022

(54) INTRAOCULAR PRESSURE SENSOR (71) Applicant: Board of Trustees of Michigan State University, East Lansing, MI (US)

(72) Inventors: Wen Li, Okemos, MI (US); Arthur J. Weber, East Lansing, MI (US); Mohammad Hossein Mazaheri Kouhani, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 262 days.

(21) Appl. No.: 16/494,894

(22) PCT Filed: Mar. 21, 2018

(86) PCT No.: PCT/US2018/023502
§ 371 (c)(1),
(2) Date: Sep. 17, 2019

(87) PCT Pub. No.: WO2018/175539
PCT Pub. Date: Sep. 27, 2018

(65) Prior Publication Data
US 2020/0015678 A1 Jan. 16, 2020

Related U.S. Application Data

(60) Provisional application No. 62/474,750, filed on Mar. 22, 2017.

(51) Int. Cl.
*A61B 3/16* (2006.01)
*A61B 5/07* (2006.01)
(Continued)

(52) U.S. Cl.
CPC .................. *A61B 3/16* (2013.01); *A61B 5/07* (2013.01); *G01L 9/0004* (2013.01);
(Continued)

(58) Field of Classification Search
CPC ..... A61B 5/6846; A61B 5/68; A61B 2562/00; A61B 5/6832; A61B 5/07;
(Continued)

(56) References Cited

U.S. PATENT DOCUMENTS 6,089,711 A * 7/2000 Blankenbecler ..... G02B 3/0087
351/159.02
7,137,952 B2 11/2006 Leonardi et al.
(Continued)

FOREIGN PATENT DOCUMENTS

CN 204218877 U 3/2015
WO WO-2014/184137 A1 11/2014
WO WO-2016071253 A1 * 5/2016 ............. G02C 11/10

OTHER PUBLICATIONS

M. H. M. Kouhani, et al, "Wireless Intraocular pressure sensor using stretchable variable Inductor", 2017 IEEE 30th International Conference on Micro Electro Mechanical Systems (MEMS), Las Vegas, NV (Feb. 28, 2017).
(Continued)

*Primary Examiner* — Patrick Fernandes
(74) *Attorney, Agent, or Firm* — Harness, Dickey & Pierce PLC (57) ABSTRACT

A pressure sensor system is provided. In another aspect, a wireless intraocular pressure sensor includes a deformable or stretchable inductor. A further aspect of an intraocular pressure sensing system includes a deformable inductor sized to contact an eye. Another aspect provides an organ pressure sending system including a passive inductor with a wavy, serpentine or undulating shape.

31 Claims, 8 Drawing Sheets

(51) Int. Cl.
*G01L 9/00* (2006.01)
*A61B 5/00* (2006.01)

(52) U.S. Cl.
CPC .......... *G01L 9/0005* (2013.01); *A61B 5/6832* (2013.01); *A61B 2562/0247* (2013.01)

(58) Field of Classification Search
CPC .... A61B 2562/0247; A61B 3/16; G02C 1/02; G02C 1/04; G02C 1/06
USPC .................................................. 600/398, 399
See application file for complete search history.

(56) References Cited

U.S. PATENT DOCUMENTS

| | | | |
|---|---|---|---|
| 9,271,677 B2 | 3/2016 | Leonardi | |
| 2009/0299216 A1* | 12/2009 | Chen ................ | A61B 5/02014 600/561 |
| 2010/0016704 A1* | 1/2010 | Naber .................... | A61B 3/16 600/398 |
| 2012/0277568 A1* | 11/2012 | Chiou .................... | A61B 3/16 600/398 |
| 2013/0184554 A1 | 7/2013 | Elsheikh et al. | |
| 2014/0243645 A1 | 8/2014 | Leonardi | |
| 2015/0073253 A1 | 3/2015 | Bouwstra et al. | |
| 2015/0087953 A1 | 3/2015 | Chlou et al. | |
| 2015/0173680 A1 | 6/2015 | Etzkorn et al. | |
| 2016/0051143 A1 | 2/2016 | Rickard et al. | |
| 2017/0280997 A1* | 10/2017 | Lai ....................... | A61B 5/6898 |

OTHER PUBLICATIONS

Chen, Po-Jui, et al.: "Implantable Micromechanical Parylene-Based Pressure Sensors for Unpowered Intraocular Pressure Sensing," Journal of Micromechanics and Microengineering, 17, Aug. 31, 2007, pp. 1931-1938.
Chen, Po-Jui: "Implantable Wireless Intraocular Pressure Sensors," Thesis—California Institute of Technology, 2009, 187 pages.
Crum, Brian, et al.: "Parlyene Based Fold-and-Bond Wireless Pressure Sensor," Department of Electrical and Computer Engineering, IEEE, NEMS2013, Suzhou, China, Apr. 7-10, 2013, pp. 1155-1158.
Deffree, Suzanne: "Researchers Claim Millimeter Scale Computing System," Pulse, EDN, Apr. 7, 2011, p. 12.
Dow Corning Product Information: Sylgard® 184 Silicone Elastomer, Apr. 2, 2014, four pages.
Katuri, Kalyan Chakravarthi: "Design and Optimization of Passive Wireless Intraocular Pressure Sensor," Dissertation—North Carolina State University, 2012, 131 pages.
Leonardi, Matteo, et al.: "First Steps Toward Noninvasive Intraocular Pressure Monitoring With a Sensing Contact Lens," Investigative Ophthalmology & Visual Science, vol. 45, No. 9, Sep. 2004, pp. 3113-3117.
MicroChem Nano™ PMMA and Copolymer Data Sheet, 2001, eight pages.
Sánchez, Irene, et al.: "Prototype of a Nanostructured Sensing Contact Lens for Noninvasive Intraocular Pressure Monitoring," Investigative Ophthalmology & Visual Science, vol. 52, No. 11, Oct. 2011, pp. 8310-8315.
Specialty Coating Systems™ brochure, 2007, 12 pages.
Sigma-Aldrich® Product Specification: Poly(3,4-ethylenedioxythiopene)-poly(styrenesulfonate)- 3.0-4.0% in H2O1 (high-conductivity grade), published prior to Mar. 2017, one page.
Supplementary European Search Report for EP 18 77 2211, dated Nov. 13, 2020.
Todani, Amit et al.: "Intraocular Pressure Measurement by Radio Wave Telemetry," Investigative Ophthalmology & Visual Science, vol. 52, No. 13, Dec. 2011, pp. 9573-9580.
"Transponder System for Measuring and Monitoring the Intraocular Pressure," Fraunhofer Institut Mikroelektronische Schaltungen und Systeme, published prior to Mar. 2017, two pages.
Yu, Lawrence, et al.: "Chronically Implanted Pressure Sensors: Challenges and State of the Field," Sensors, ISSN 1424-8220, Oct. 31, 2014, pp. 20620-20644.

\* cited by examiner

INTRAOCULAR PRESSURE SENSOR

CROSS-REFERENCE TO RELATED APPLICATIONS

This application is a National Phase Entry of International Application Serial No. PCT/US2018/023502, filed on Mar. 21, 2018, which claims the benefit of U.S. Provisional Application No. 62/474,750 filed on Mar. 22, 2017 both of which is are incorporated by reference herein.

BACKGROUND AND SUMMARY

The present disclosure relates generally to pressure sensors and more particularly to a wireless intraocular pressure sensor system including a deformable inductor.

Glaucoma is the second leading cause of blindness which is an asymptomatic, progressive and irreversible disease that is usually associated with elevated intraocular pressure. Most conventional constructions of intraocular pressure sensors can be categorized into three general groups in terms of their energy transferring mechanisms: active, passive, and radio-frequency-powered devices.

Active devices traditionally employ application specific integrated circuits that can store, process and transmit data. However, they make the overall device large, heavy and inflexible. Furthermore, such active systems typically require an integrated battery or power-receiving coil, which both add to the weight and size of the device.

Traditional passive sensors require high precision surgery to anchor the device to the iris. The fabrication process for such passive devices is typically complex and expensive. Furthermore, such traditional passive sensors require an external reading mechanism of an undesirably large size that interferes with the vision of the patient thereby making it unsuitable for wearable long term measurements.

Conventional radio frequency or electromagnetic coupled sensors have employed variable capacitors to sense pressure. These variable capacitors, however, require a pressurized reference chamber that has great difficulty in sustaining its baseline pressure over time due to packaging imperfections. This causes significant undesirable signal drift due to the leakage.

Exemplary prior intraocular pressure sensors are disclosed in U.S. Pat. No. 9,289,123 entitled "Contact Lens for Measuring Intraocular Pressure" which issued to Weibel et al. on Mar. 22, 2016, and U.S. Patent Publication No. 2016/0051144 entitled "Systems and Methods for Monitoring Eye Health" which published to Rickard et al. on Feb. 25, 2016. Both of these are incorporated by reference herein. It is noteworthy that Weibel includes a considerable quantity of electronic components. Moreover, Rickard uses only capacitive sensing and requires surgical implantation into the eye.

In accordance with the present invention, a pressure sensor system is provided. In another aspect, a wireless intraocular pressure sensor includes a deformable or stretchable inductor. A further aspect of an intraocular pressure sensing system includes a deformable and variable inductor, within a ring-shaped carrier layer, sized to contact an eye. Another aspect provides an organ pressure sensing system including a passive inductor with a wavy, undulating or serpentine shape. In yet another aspect, a biomedical pressure sensor includes a deformable inductor having an undulating pattern along at least a majority of its length, a deformable outer ring spaced away from and surrounding the inductor, and elongated connectors or arms spanning between the inductor and an outer ring, with the connectors being radially elongated and causing deformation of an adjacent portion of the inductor when the outer ring is deformed or moved due to internal body pressure. A method of making and/or using a wireless intraocular pressure sensor, including a deformable inductor, is also provided.

The present pressure sensor is advantageous over conventional devices. For example, the present pressure sensor functions as a passive strain gauge that synergistically serves as both a pressure sensitive element and a wireless communications interface. It advantageously does not obstruct the vision of the patient, as compared to conventional cornea-mounted devices. Furthermore, in one exemplary construction, the present system is intended to be a temporarily worn device that is easily removable or dissolvable after a pre-determined period of time, and does not require surgical in vivo implantation or removal. Another exemplary construction in vivo implants only a passive sensor for use with a portable or temporarily adhered reader. Moreover, the present system advantageously includes only minimal electronic components, such as a single capacitor, located in the sensor device inserted onto the eye; this provides a much lighter weight and lower cost device which does not obstruct the patient's vision. Additional advantages and features of the present system and method will become apparent from the following description and appended claims, taken in conjunction with the associated drawings.

DETAILED DESCRIPTION

A first embodiment of an intraocular pressure sensing system 21 is shown in FIGS. 1-8, and includes an intraocular pressure sensor 23 and a reader 25. Sensor 23 includes a sensing and transmitting coil assembly 27, an outer ring 29 and a plurality of connecting arms 31 spanning between the spaced apart coil assembly 27 and outer ring 29. Coil assembly 27 has a looped metallic inductor 33 at least partially encapsulated within a protective polymeric layer or casing 35. Inductor 33 is preferably made from layers of titanium and copper, titanium and gold, or an alloy thereof. Alternately, other metallic or conductive polymeric materials may be employed although they may not be as advantageous.

Figure 5:
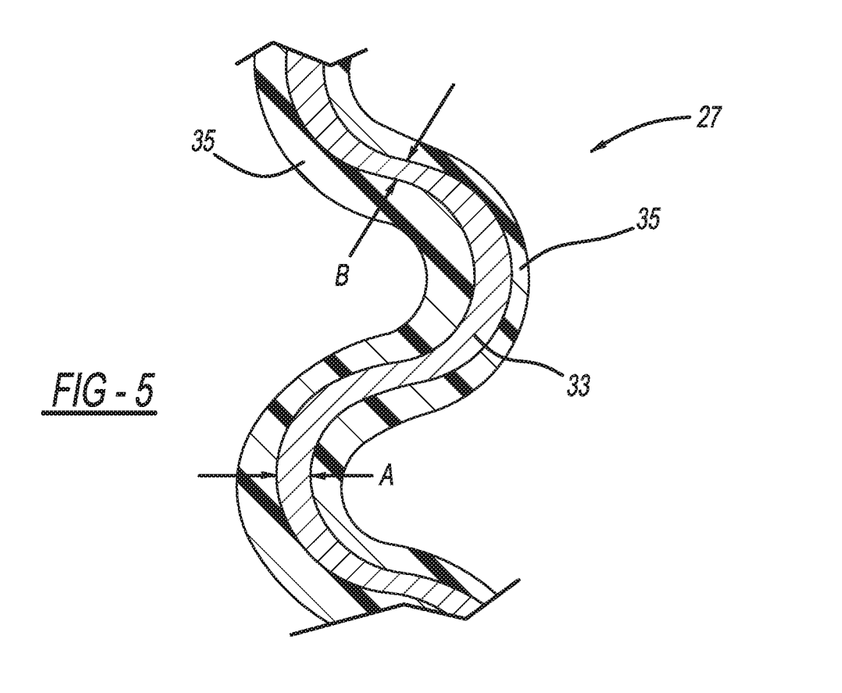
FIG. 5 is a longitudinal sectional view, taken along line 5-5 of FIG. 3, showing the first embodiment present intraocular pressure sensor.

Inductor 33 and protective layer 35 have an undulating, serpentine or wave-like shape along a curved length thereof, defined by alternating peaks and valleys with curved diagonal walls connecting therebetween. As will be described in greater detail hereinafter, the undulating shape allows inductor 33 to be deformed and stretchably expanded at any point therealong. FIG. 5 illustrates an increased width A of the inductor at each peak and valley which is greater than width B at each of the diagonal connecting walls. This effectively adds increased material at the peak and valley areas which are more prone to fracture when expanded or deformed. However, an eye-facing inner surface 41 and an opposite outer surface 43 of inductor 33 are preferably substantially flat. Furthermore, the corresponding eye-facing inner surface 45 and opposite outer surface 47 of protective layer 35 are preferably substantially flat, but for optionally curved corners.

At least three and more preferably at least four connecting arms 31 are spaced away from each other with open gaps 51 therebetween. Each connecting arm 31 is radially elongated away from a center point of sensor 23. Moreover, each connecting arm 31 is integrally and directly connected to an outer periphery of protective layer 35 of sensor 27 and to an inside diameter surface 53 of outer ring 29. Each connecting arm 33 is preferably at least five times as long as wide C and at least twice as wide C as thick D. This dimensional arrangement allows connecting arms 31 to have a partially spherical or curved side view shape between their opposite ends to match the eye's shape. This dimensional configuration also allows for torsional flexure with minimal linear or radial stretch of the connecting arms. Notwithstanding, these exemplary dimensions may be varied.

Outer ring 29 preferably has a circular or arcuate outer periphery 55. A width E of outer ring 29 is preferably at least five times width C of each connecting arm 31 and at least ten times that of coil assembly 27. Notwithstanding, these exemplary dimensions may be varied. Outer ring 29 and coil assembly 27 are coaxial with gaps 51 therebetween. Multiple apertures 57 are disposed through the thickness of outer ring 29 for mechanically receiving and interlocking with a biocompatible adhesive applied to temporarily hold outer ring 29 to a sclera 59 of eye 61. The polymeric material for outer ring 29, connecting arms 39 and protective layer 35 is preferably Parylene-C (obtained from Parylene Coater-Specialty Coating System as PDS 2010), Sylgard® 184 Silicone Elastomer (obtained from Dow Corning), Polymethyl Methacrylate (obtained from MicroChem Corporation)) or the like.

A single electrical component, preferably a capacitor 63, is electrically connected to ends of inductor 33 and secured to sensing coil assembly 27. This is preferably the only electronic component directly attached to sensor 23, such that a battery, microprocessor and other solid state electrical components are not required, thereby saving weight and reducing cost.

Figure 2:
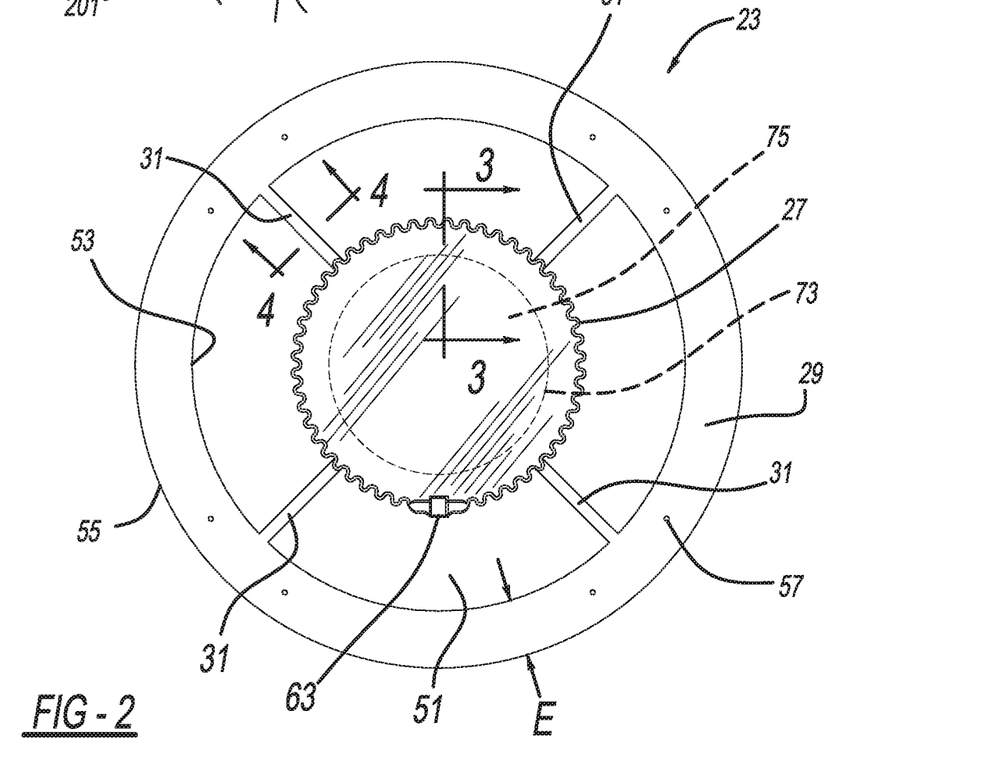
FIG. 2 is a front elevational view showing the first embodiment of an intraocular pressure sensor of the present system.
Figure 3:
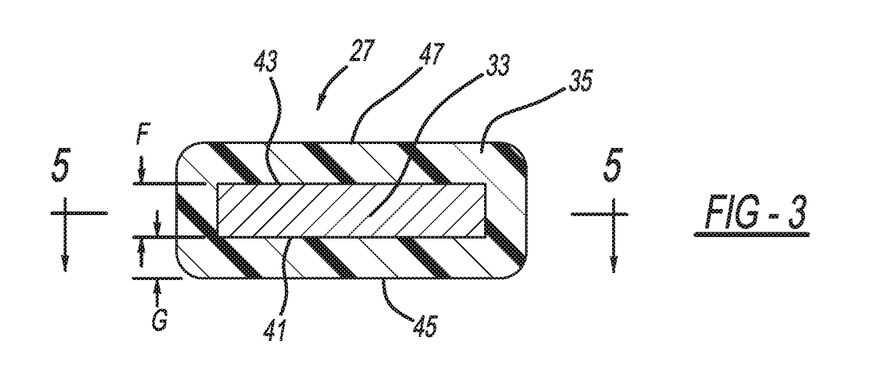
FIG. 3 is a cross-sectional view, taken along line 3-3 of FIG. 2, showing the first embodiment present intraocular pressure sensor.
Figure 4:
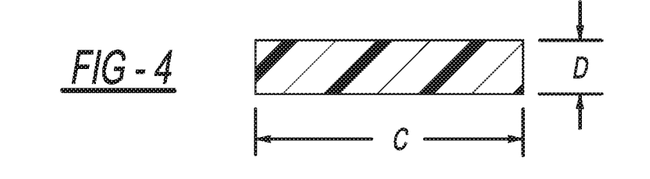
FIG. 4 is a cross-sectional view, taken along line 4-4 of FIG. 2, showing the first embodiment present intraocular pressure sensor.
Figure 7:
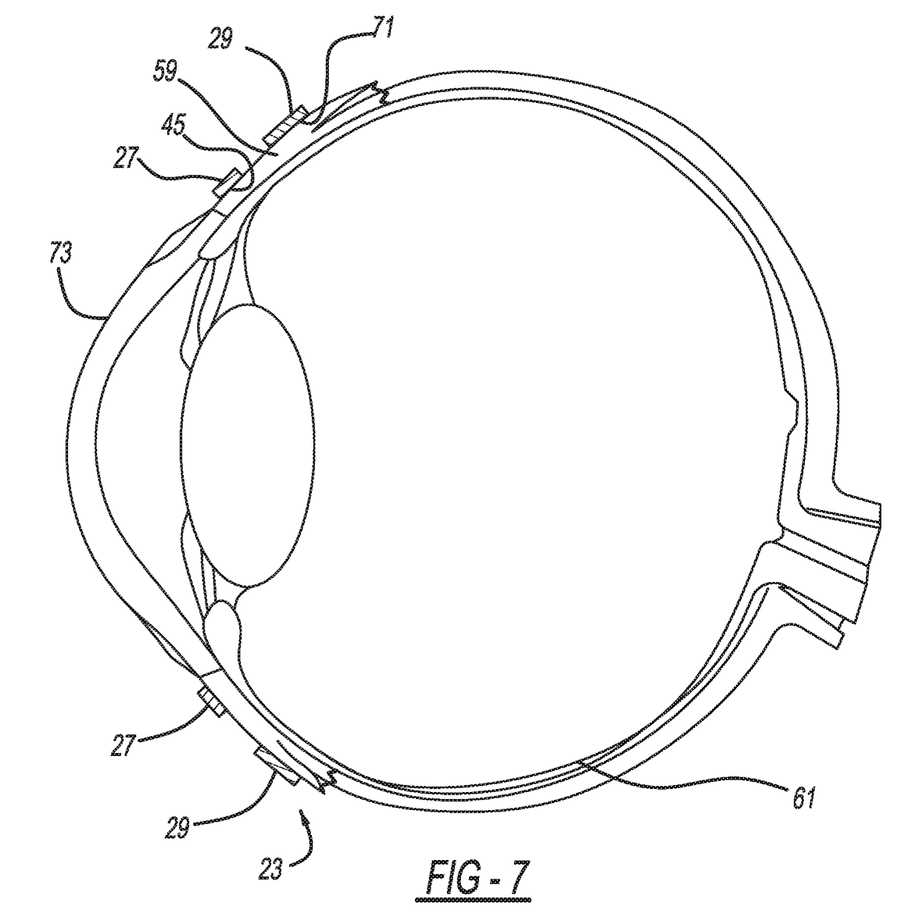
FIG. 7 is a cross-sectional view showing the first embodiment present intraocular pressure sensor on an eye.

The placement of sensor 23 relative to an organ, specifically a patient's eye 61, can best be observed in FIGS. 2 and 7. An inner surface 71 of outer ring 29 is temporarily mounted to sclera 59 by a dissolvable adhesive such as a hydrogel based adhesive. Inner surface 71 may optionally have a partial dome shape to conform to the sclera. Connecting arms 31 and sensing coil assembly 27, however, are free of an adhesive and allowed to move relative to eye 61. Sensing coil assembly 27, connecting arms 31 and outer ring 29 are all external to and outside of a periphery of a cornea 73 of eye 61. Nevertheless, an optional dissolvable polymeric film 75, of a generally dome-like shape, spans between an inside edge of sensor coil assembly 27 and initially spans across cornea 73. This optional central film 75 is simply intended to add temporary supporting structure to the thin and deformable sensing coil assembly 27 during user or doctor insertion onto the eye and is intended to dissolve away within a day or two thereafter such that there is an unobstructed central opening over the cornea during normal sensing use. Outer ring 29, connecting arms 31, protective layer 35 and optional central film 75 are all substantially transparent.

Figure 1:
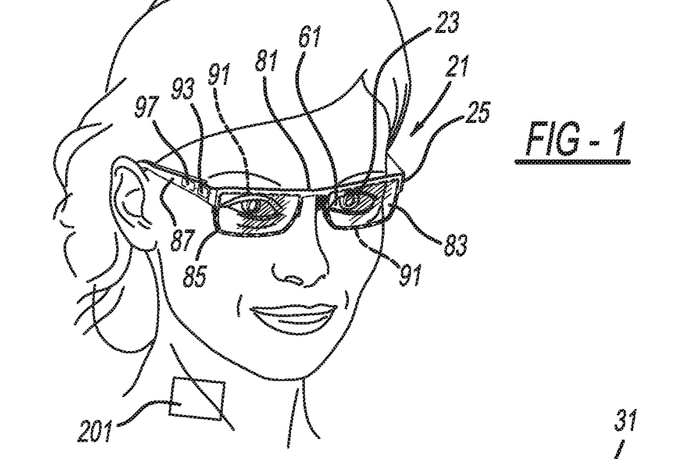
FIG. 1 is a perspective view showing a first embodiment of the present intraocular pressure sensor system as worn on a patient.
Figure 6:
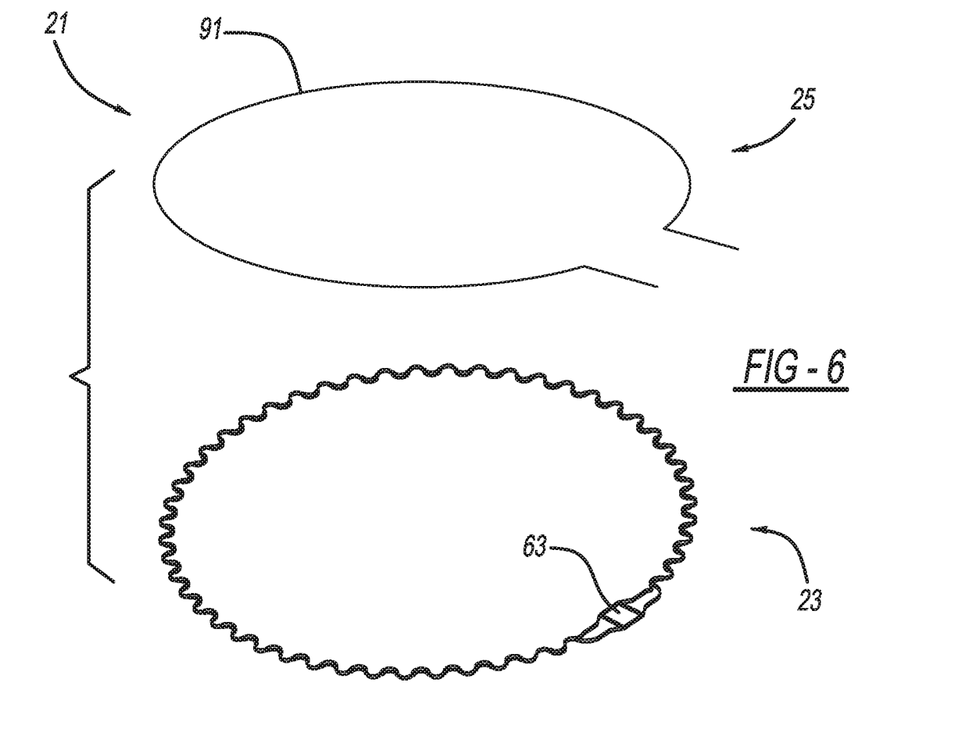
FIG. 6 is a diagrammatic and exploded perspective view showing the first embodiment present intraocular pressure sensor system.
Figure 8:
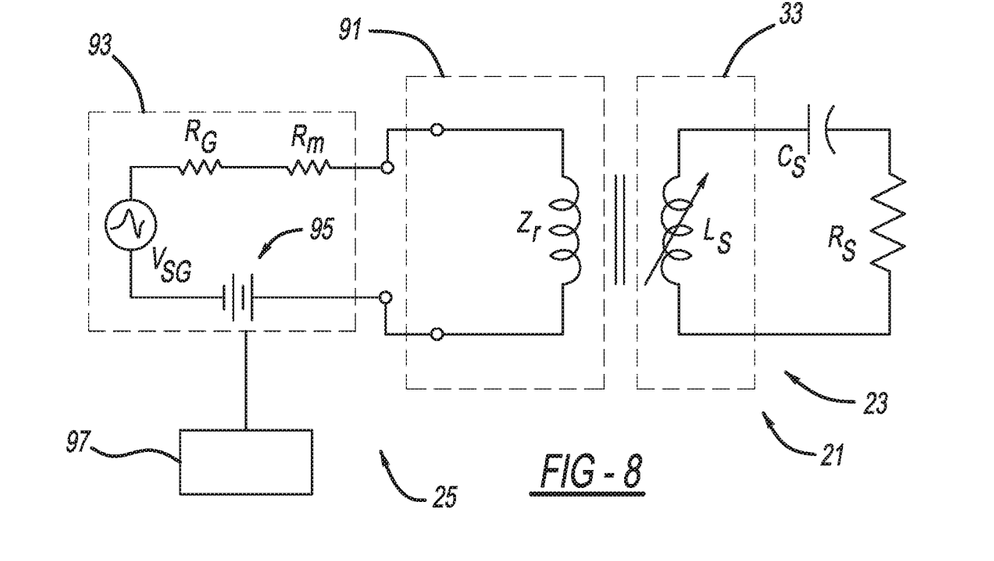
FIG. 8 is a circuit diagram of the first embodiment present intraocular pressure sensor system.

Referring now to FIGS. 1, 6 and 8, reader 25 is preferably mounted to eyeglasses 81 which include transparent lenses 83, a frame 85 and earpieces 87. A reading coil or wire 91 is encapsulated within or adhered to an inside surface of eyeglass frame 85 generally surrounding each lens 83. Ends of the looped reading coil 91 are electrically connected to an electrical circuit 93 including a battery 95 for a wearable/portable reader or other power supply accessed through a wall outlet plug for a stationary reader, a signal generator voltage source ($V_{SG}$), a signal generator internal resistor ($R_G$), and a measurement resistor ($R_M$). In the circuit diagram, reading coil 91 is shown as a receiver coil impedance inductor ($Z_r$). Further in the circuit diagram of FIG. 8, constant capacitor 63 is shown as $C_S$, a parasitic resistor function of the inductor is shown as $R_S$, and variable inductor 33 is illustrated as $L_S$.

Periodic electromagnetic transmissions are sent from the reader coil to the passive sensor coil to activate a resonant frequency of the sensor coil. This resonant frequency is based on the geometries of the inductor and capacitor, and has an exemplary frequency of 100 MHz to 1 GHz, which can be varied depending on the detectable frequency range of the impedance analyzer. Readout signals of the reader coil are impedance amplitude and phase over this frequency range to characterize the resonant frequency, where a phase dip is observed if the inductor is deformed. The phase dip is an indicator of the resonant frequency such that when the sensing inductor is deformed in response to pressure variation, a frequency shift of this phase dip can be detected.

Referring now to FIGS. 2 and 6-8, if intraocular pressure outwardly bulges or expands sclera 59 of eye 61 then outer ring 29 of sensor 23 will move off its nominal inner surface 71 position and/or radially move from its nominal circular position. This will move at least one of the adjacent connecting arms 31 in a linear and/or torsional manner. This movement of connecting arm 31 will subsequently deform, flex or circumferentially expand inductor 33 away from its nominal free position which will accordingly change an inductance value received by reader coil 91 from inductor 33. The sensor serves as a planar and circular LC passive resonator that has a constant capacitor and a stretchable variable inductor. The self-inductance of the inductor, the parasitic capacitance between the segments, and the Q-factor are all changeable by the expansion of the sensor diameter. In addition, the mutual inductance between the sensing coil and reader coil will also change as the sensing coil deforms. This phenomenon is employed to measure the strain and the eye tissues induced by intraocular pressure elevation. Accordingly, the change of self-inductance in parasitic capacitance results in the change of resonance frequency of the LC loop. Therefore, the pressure variance can be read by the impedance analyzer through a frequency drift. The resultant output from impedance analyzer 93 of reader 25 is transmitted via communications transmitter 97 to a handheld or stationary computer device, through a Bluetooth standard, a Wi-Fi standard, an RFID standard, a ZigBee standard or the like. This sensor deformation provides an advantageous method of use.

Figures 9A, 9B:
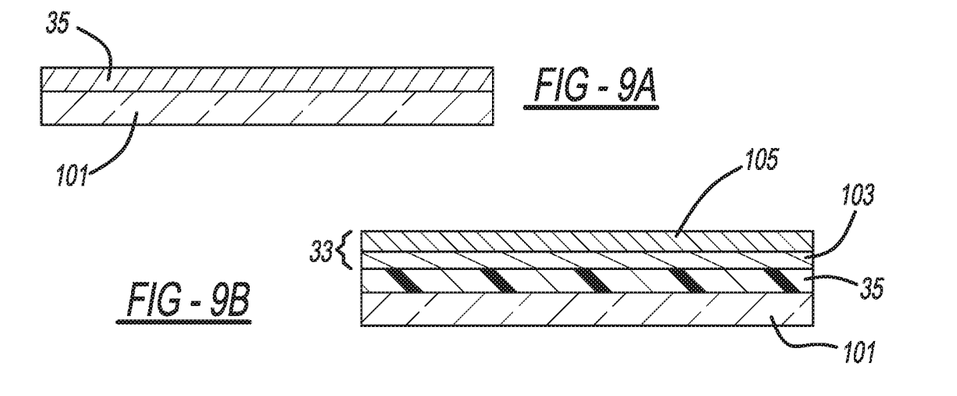
FIG. 9A-H are a series of cross-sectional views showing a manufacturing process for the present intraocular pressure sensor for all embodiments.
Figure 9C:
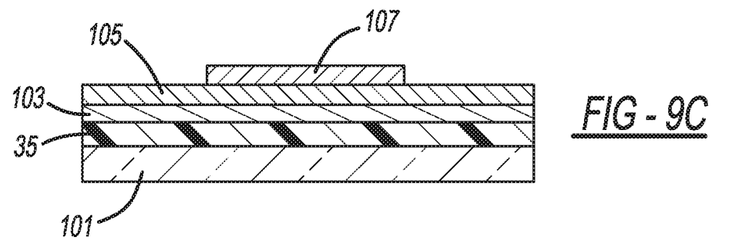
Figures 9D, 9E:
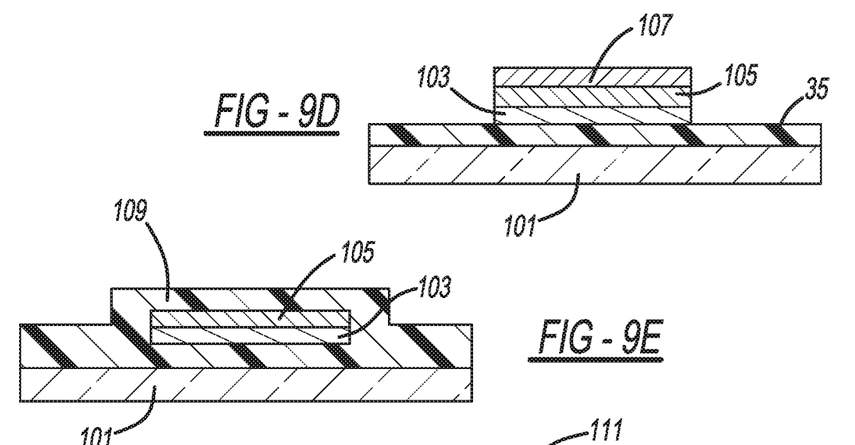
Figures 9F, 9G, 9H:
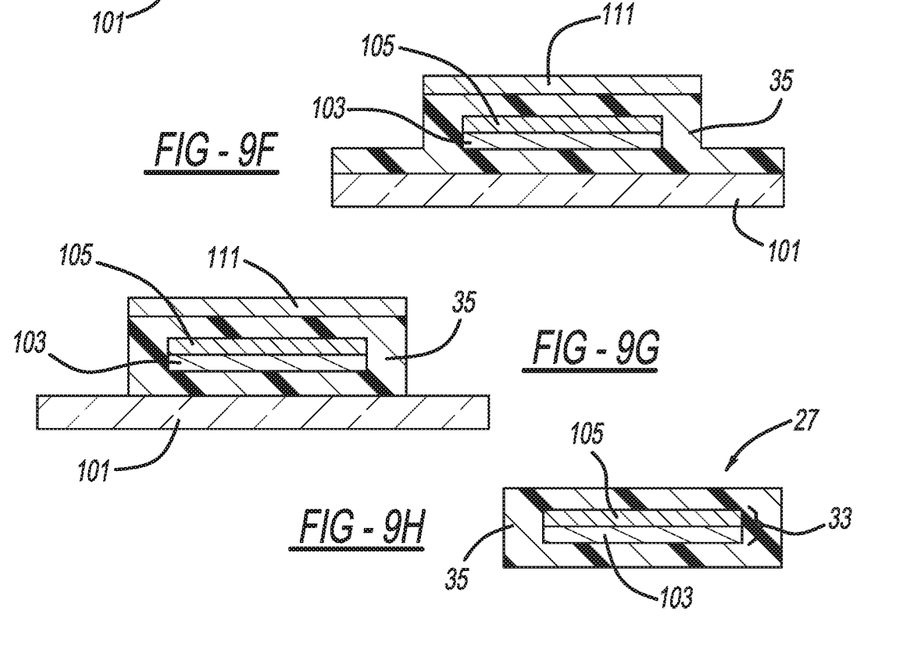

A preferred manufacturing or fabrication process for at least the sensing coil assembly 27 portion of sensor 23 is illustrated in FIGS. 9A-H. Two masks are employed. As shown in FIG. 9A, polymer 35 is deposited in a chemical vapor deposition process. First, a glass wafer or substrate 101 is coated with five μm of Parylene-C polymer 35, a twenty nm layer of titanium and a 700 nm layer of copper, 103 and 105 respectively, which will become inductor 33. This is shown in FIG. 9B. Second, metallic layers 103 and 105 are evaporated using a thermal evaporator. A photoresist layer 107 or first mask is used to pattern the undulating shape using ultraviolet photolithography and thereafter wet-etching as illustrated in FIGS. 9C and 9D. Third, photoresist layer 107 is subsequently added on top of the copper layer 105. Fourth, surface mounted capacitor 63 (see FIG. 2) is soldered to the end contacts of inductor 33 using silver epoxy. Fifth, FIG. 9E illustrates applying another five μm polymeric coating at 109 to fully encapsulate the inductor layers. Sixth, FIG. 9F shows a layer of aluminum 111 deposited on top of outermost polymeric layer 109 and patterned using a second photoresist layer mask to form an aluminum mask that protects the sealed metallic inductor core during subsequent plasma dry etching of the polymeric casing to create the trimmed form shown in FIG. 9G. Finally, FIG. 9H shows the completed sensing coil assembly 27 separated from the glass substrate and with the aluminum mask removed. The connecting arms and outer ring are also simultaneously formed in an integral and one piece manner with the polymeric encapsulating layers.

The completed inductor preferably has a thickness F (see FIG. 3) of approximately 500-900 nm and more preferably 720 nm. A thickness G of protective polymeric layer 35 on each inner and outer surface is approximately 3-10 μm and more preferably 4-5 μm. Alternately, the inductor and/or polymeric layers can be two-dimensionally or three-dimensionally printed. Furthermore, the polymeric material may alternately be coated onto the metallic inductor by spinning, chemical vapor deposition, dipping at room temperature, or spraying. Moreover, the inductor may alternately be produced by using 2-D printing, e-beam evaporations, vapor deposition, sputtering, electroplating or electroless plating.

Figures 10, 11, 12:
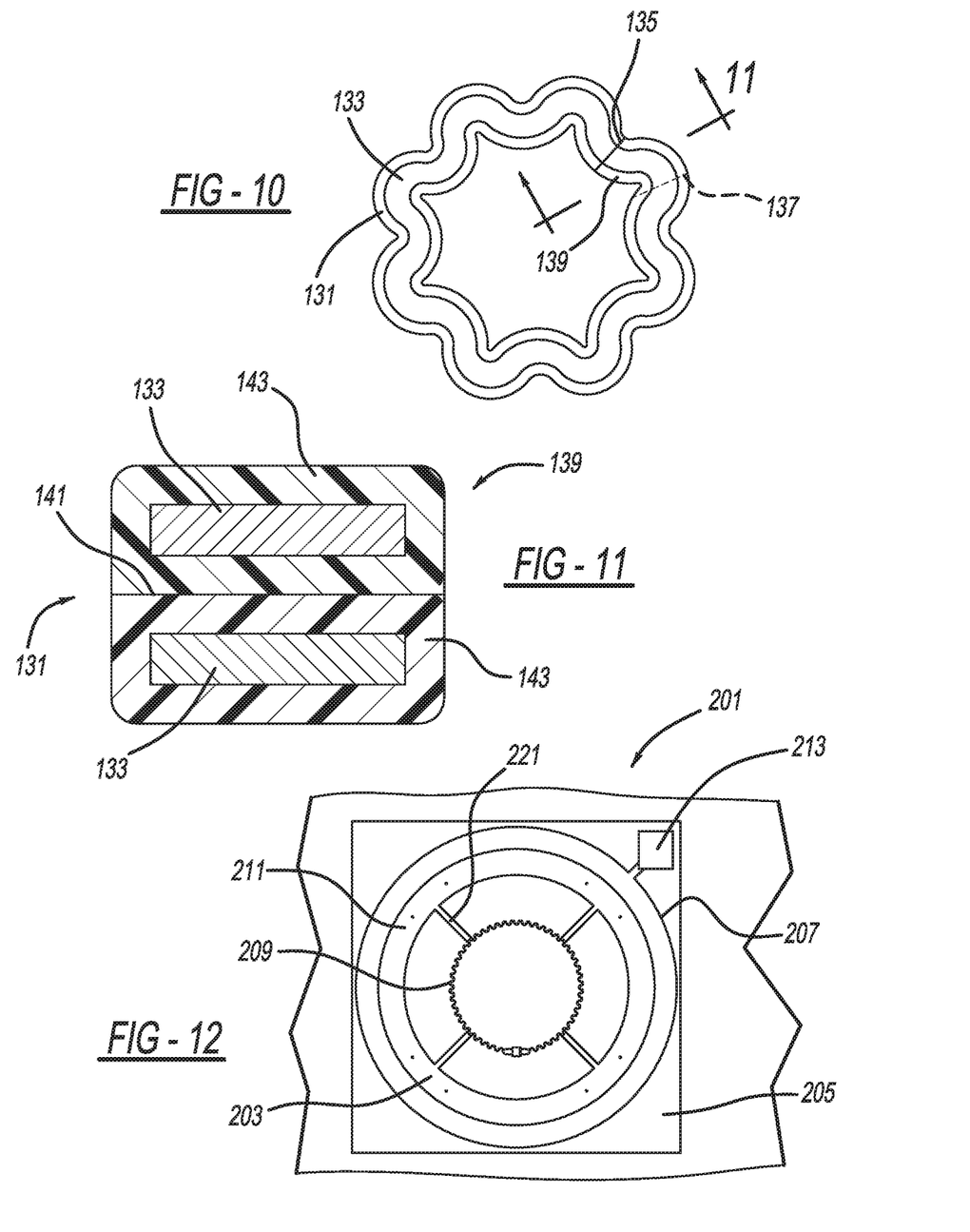
FIG. 10 is a front elevational view showing an alternate embodiment of the present intraocular pressure sensor.
FIG. 11 is a cross-sectional view, taken along line 11-11 of FIG. 10, showing the alternate embodiment intraocular pressure sensor.
FIG. 12 is a front-elevational view showing another alternate embodiment intraocular pressure sensor system.

Reference should now be made to FIGS. 10 and 11 for an alternate embodiment of the present pressure sensor. In this construction, a generally annular sensing coil assembly 131 includes an undulating inductor coil 133 at least partially encapsulated in a protective polymeric casing or layer 143. Connecting arms and an outer ring such as in the prior embodiment are also included although not presently shown. Ends 135 and 137 of sensing coil assembly 131 extend past each other such that distal segments 139 overlap each other in a stacked manner with an adhesive therebetween to secure together internal facing surfaces 141 thereof.

If an adhesive is not employed in a variation thereof, the integrated sensing inductor and capacitor can be microfabricated using a metal-polymer sandwich. Such can be manufactured by: first, depositing a polymeric bottom layer; second, depositing and patterning a bottom metal plate layer of the capacitor; third, deposition and patterning of a polymeric dielectric layer on top of the metal plate; fourth, depositing and patterning a top metal plate layer; then fifth, encapsulating the top capacitor plate within a polymeric material.

Polymeric layer 143 encapsulating inductor 133 serves as a predominantly non-conductive insulator between the overlapped ends of inductor 133 at overlapping segment 139. Thus, overlapping segment 139 functions as a capacitor integrated as a synergistic and multifunctional construction along with the sensing inductance and signal transmitting antenna-like functions. The microfabricated version advantageously eliminates the capacitor assembly steps and improves device reliability and production yield. Accordingly, a separate capacitor component is not required. It should be appreciated that while it is preferred to use this integrated inductor and capacitor device for a wireless intraocular pressure sensor, it should also be appreciated that this device may alternately be applied to a variety of other types of biomedical sensors that are attached to or implanted in a patient.

FIG. 12 illustrates yet another alternate embodiment biomedical pressure sensor 201. In this exemplary configuration, sensor system 201 includes a passive sensor 203 essentially the same as with the first embodiment of FIG. 2, however, it is mounted to an internal patient-side or encapsulated within a patch 205. Patch 205 is preferably a flexible film or sheet of polymeric material with a pressure sensitive adhesive on the internal side thereof. Furthermore, a looped reading coil wire 207 is attached to one of the surfaces of patch 205 or encapsulated therein. Reading coil wire 207 coaxially surrounds inductor 209 and an outer ring 211 without directly contacting inductor 209. Impedance analyzer and communications circuitry 213 and associated electronics are electrically connected to reading coil wire 207 and mounted to an outside surface of patch 205. As shown in FIG. 1, sensor system 201 is removably adhered to external skin area of the patient so as so sense blood pressure, heart rate, or other patient-induced movements which deform the outer ring, connecting arms 221 and the inductor.

An alternate design employs a wearable sensing watch with the impedance analyzing circuitry and a digital display constructed on an outside surface of a patch, which is electrically connected to a reading coil wire. The watch is wrist mounted by a strap, and includes a timekeeping clock circuit in addition to the reading circuit, but is otherwise like that shown in FIG. 12. In this construction, there is no need for communications circuitry to transfer data to a separate reader.

Figure 13:
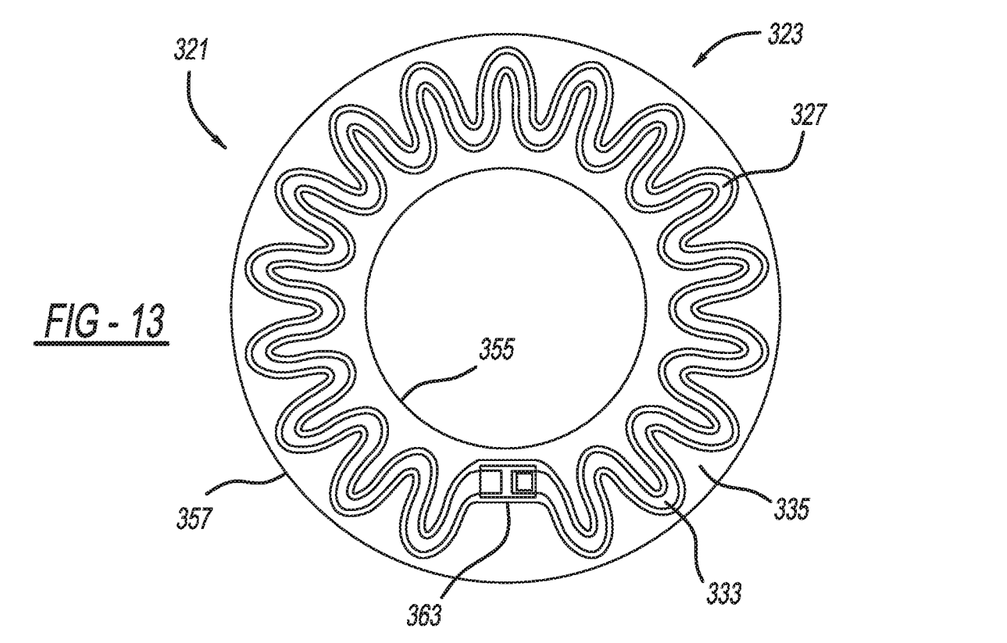
FIG. 13 is a front elevational view showing a second embodiment of an intraocular pressure sensor of the present system.
Figure 14:
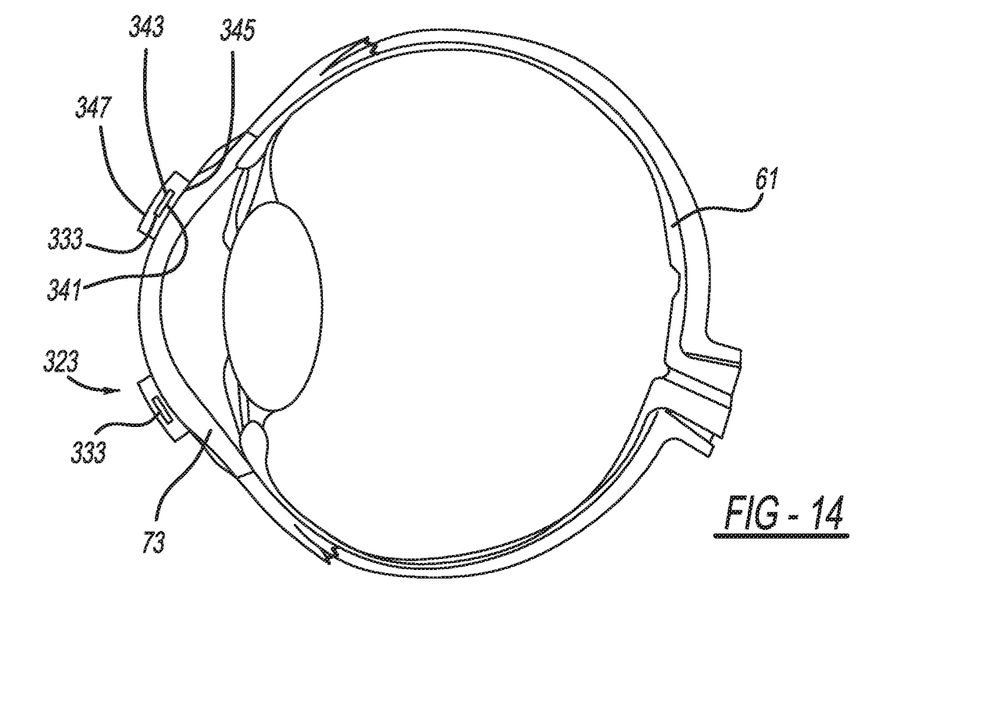
FIG. 14 is a cross-sectional view showing the second embodiment present intraocular pressure sensor on an eye.

A second major embodiment of an intraocular pressure sensing system 321 is shown in FIGS. 13 and 14, and includes an intraocular pressure sensor 323 used with the previously disclosed reader 25 (see FIG. 1). Reader 25, however, includes an analog front-end circuit for impedance measurements and a user friendly control panel or display, in addition to a conductive coil, a microprocessor controller and a power supply like a battery.

Sensor 323 includes a sensing and transmitting coil assembly 327 embedded in a donut shaped or ring-like carrier or protective layer 335. Protective layer 335 has concentric inner and outer edges 355 and 357, respectively. Coil assembly 327 has a looped metallic inductor 333 at least partially encapsulated within protective and insulating layer 335 which is polymeric. Inductor 333 is a variable inductor.

Inductor 333 has an undulating, serpentine or wave-like shape along a curved length thereof, defined by alternating peaks and valleys with curved diagonal walls connecting therebetween. The undulating shape allows inductor 333 to be deformed and stretchably expanded at any point therealong. The materials and manufacturing process for this exemplary inductor and protective layer can optionally be the same as for the first embodiment. Alternately, coil assembly 327 is optionally placed into a mold designed for the size and curvature of the cornea to which it will be applied. The mold is thereafter filled with a polymer (e.g., PDMA, PDMS or HEMA) and the material is polymerized by heating or exposure to UV light to create the desired final shape for carrier layer 335.

An eye-facing inner surface 341 and an opposite outer surface 341 of inductor 333 are preferably substantially parallel to each other and flat. Furthermore, the corresponding eye-facing inner surface 345 and opposite outer surface 347 of protective layer 335 are preferably substantially parallel to each other, and may optionally include curved corners and curved intersecting sides. Eye-facing inner surface 345 of protective layer 335 contacts against and is positioned over cornea 73 of eye 61 adjacent a periphery thereof. If intraocular pressure outwardly expands and stretches the cornea, this stretching will subsequently deform, flex or circumferentially expand inductor 333 away from its nominal free position which will accordingly change an inductance value received by the reader coil from inductor 333.

The electrical circuit function of the second embodiment organ sensing system 321 is similar to that shown in FIG. 8. The present use of a variable inductor in an LCR tank, parallel resonance circuit for strain sensing is incorporated for intraocular organ pressure sensing. It employs a flexible and stretchable conductive element which is achieved using serpentine geometry. The capacitance in series with the inductor is achieved on-chip and is a constant capacitor in the range of 5 picoFarads (for both the capacitor 363 in FIGS. 13 and 63 in FIG. 2). The inductor diameter is near 11 millimeters that results in a variable inductor near 35 nano Henries. The parasitic resistance is below 10 ohms that results in a good quality factor. Furthermore, the mean resonance frequency of the LCR tank is near 500 Megahertz. It should be appreciated, however, that these specific exemplary values will be optimized for different organ applications, and therefore, may vary. The stretchable inductor is placed around the corneoscleral joint and the sensor stretches and changes the inductor's diameter when elevation of intraocular pressure changes the circumferential curvature of the cornea. The curvature change is transferred to the stretchable inductor partially through the carrier layer that holds and packages the inductor inside, without the need for supplemental hermetic packaging of electronics.

Figure 15:
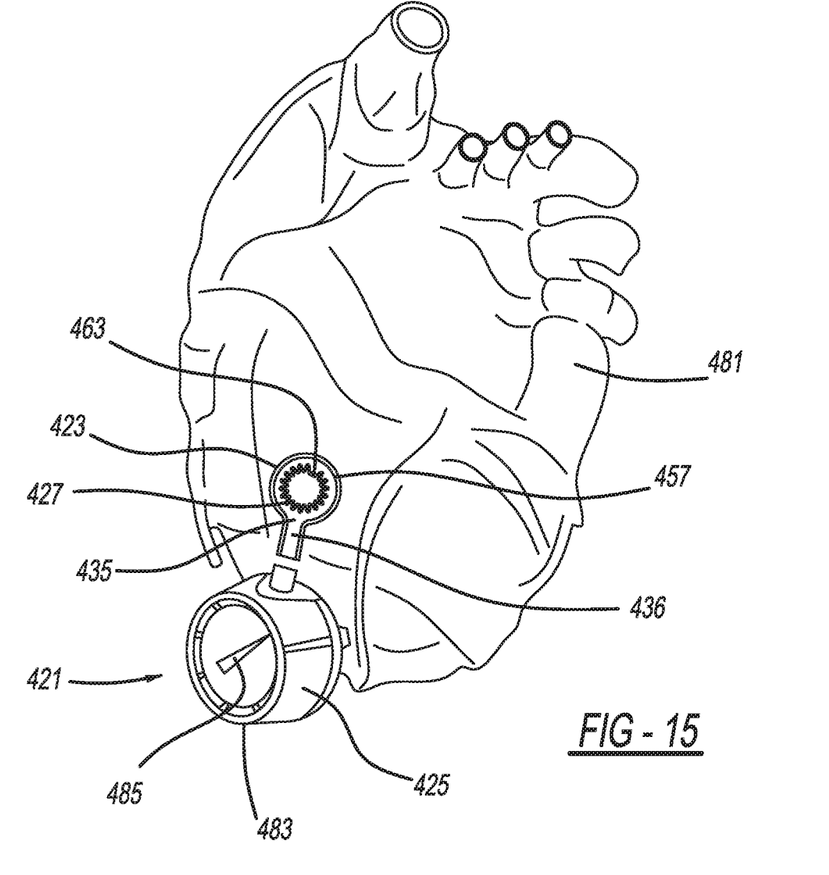
FIG. 15 is a perspective view showing a third embodiment of a cardiovascular pressure sensor system.

Another alternate embodiment is illustrated in FIG. 15. This construction employs a pressure sensing system 421 including an in vivo organ pressure sensor 423 and an ex vivo reader 425. Sensor 423 has a sensing and transmitting coil assembly 427 embedded and encapsulated in an insulating polymeric protective carrier or layer 435. This layer 435 may have an inner edge defining a central opening or may be solid, continuously spanning across the central area as is illustrated. An elongated tail 436 may optionally extend from a peripheral and generally circular and arcuate outer edge 457 of layer 435.

Coil assembly 427 includes a looped or serpentine wavy metallic inductor, and a capacitor electronic component 463 attached thereto. Sensor 423 is passive, without a microprocessor or battery attached thereto. Layer 435 is adhesively bonded to an outside surface of a cardiovascular organ 481, such as a heart or blood vessel, by a bioadhesive or less preferably, sutured thereto.

Reader 425 is a handheld and portable impedance analysis unit or module (as illustrated) within a housing 483 containing a battery power supply, microprocessor, reading coil and electrical circuit, as with the first embodiment. An analog output display dial 485 or digital display screen with numeric values may also be employed. Reader is removably placed against the patient's skin to activate sensor 423 remotely located therefrom, and to obtain a pressure measurement therefrom. Alternately, a removable adhesively bonded reader, like that shown as 201 in FIG. 1, may be employed with in vivo sensor 423.

Reader 425 employs a secondary inductor integrated to an impedance analysis circuitry, where the phase of the readout coil shows a 'dip' nearby the resonant frequency of the sensor. Impedance measurements can use various methods such as a bridge method, resonant method, I-V method, RF I-V method, network analysis method and auto balancing bridge method. Preferably, an I-V method is employed for the reader electrical circuit. This method provides high accuracy and a wide impedance range at higher frequencies like 500 MHz. It applies an electrical current to a reference impedance in series with the readout coil and measures the voltage across the readout coil within a specific frequency range that covers the resonant frequency of the sensor. The coupling coefficient between the sensor and the readout coil is reflected to the readout impedance and measured by the module.

While various embodiments of the present sensor system have been disclosed, it should be appreciated that other variations may be made. For example, alternate electrical circuits and electronic components may be used although some of the present benefits may not be realized. Furthermore, different materials and manufacturing process steps can be used, however, certain of the present benefits may not be achieved. For example, the sensing coil assembly and protective layer may be entirely made from biodissolvable material such that the sensor does not need to be manually removed from the eye. The features of any of the embodiments may be mixed and matched in an interchangeable manner with any of the other embodiments disclosed herein. Various changes and modifications are not to be regarded as a departure from the spirit or the scope of the present invention.

The invention claimed is:
1. An organ pressure sensing system comprising:
   a sensor comprising a passive inductor having a stretchable undulating shape which is elongated to create at least a majority of a circle;
   a polymeric protective layer encapsulating the passive inductor;

the sensor having an unobstructed central opening coaxial with the passive inductor when sensing;

the polymeric protective layer having an uninterrupted inner polymeric segment between an inner surface of the passive inductor and an inner edge of the polymeric protective layer, the inner surface of the passive inductor including innermost peak surfaces located adjacent to but spaced away from the inner edge; and the polymeric protective layer having an outer segment between outermost peak surfaces of the passive inductor and a peripheral outer edge, the outermost peak surfaces being located adjacent to but spaced away from the outer edge.

2. The system of claim 1, wherein the outer edge of the polymeric protective layer is circular.

3. The system of claim 2, wherein the inner edge of the polymeric protective layer is circular and defines the unobstructed central opening, and the unobstructed central opening being configured for placement over an entire cornea when the sensor is configured to be externally mounted to an eye.

4. The system of claim 1, further comprising only a single electronic component secured to the sensor.

5. The system of claim 4, wherein the electronic component is a capacitor and the capacitor is part of a parallel resonance circuit.

6. The system of claim 1, wherein the sensor is free of a microprocessor or battery, and the passive inductor is a variable inductor.

7. The system of claim 1, wherein the sensor is configured for removable placement on a human eye, the sensor has an open center configured for placement coaxial with a pupil center point of the eye, and the sensor is configured to be removably and externally mounted to the eye without surgical implantation.

8. The system of claim 1, wherein the sensor is adapted for placement on an external surface of a cardiovascular organ, and the passive inductor is a single loop.

9. The system of claim 1, further comprising a reader including a reading coil, the reader being spaced away from the sensor and being spaced away from an organ.

10. The system of claim 1, wherein the sensor is configured to be removably and externally mounted to an eye without surgical implantation.

11. The system of claim 1, further comprising:
(a) the passive inductor being configured to be located at an eye sclera surrounding outside a periphery of an eye cornea;
(b) a polymeric deformable outer ring spaced away from and surrounding the passive inductor, the outer ring being adapted to contact an external surface of the eye sclera; and
(c) elongated connectors spaced apart from each other and radially spanning between the passive inductor and the outer ring.

12. The system of claim 1, wherein the passive inductor is a single loop.

13. The system of claim 1, wherein the passive inductor has a continuously undulating and stretchable shape along a substantially circular length thereof between overlapping end portions, and lateral dimension of the passive inductor is greater than a thickness of the passive inductor.

14. The system of claim 13, further comprising a polymeric intermediate layer located between the overlapping end portions of the passive inductor, the polymeric intermediate layer and the overlapping end portions being stacked in a direction perpendicular to an eye-contacting surface of the sensor, and the overlapping end portions and the polymeric intermediate layer being a capacitor.

15. The system of claim 1, further comprising a dissolvable polymeric film spanning across the central opening.

16. An organ pressure sensing system comprising:
(a) an intraocular sensor including a passive metallic inductor within a polymeric carrier,
 (i) the inductor having an elongated and stretchable wavy shape with alternating curved peaks and valleys,
 (ii) the wavy shape of the inductor configured to surround an eye pupil centerpoint,
 (iii) the sensor being configured to be removably and externally mounted to an eye without surgical implantation,
 (iv) the inductor being a single loop of no greater than 360 degrees, and
 (v) the polymeric carrier including an outer segment between the peaks and an outer edge of the carrier, the peaks being spaced away from the outer edge;
(b) a reader including a conductive coil, a microprocessor and a power supply; and
(c) the reader being spaced away from the sensor and the organ.

17. The system of claim 16, further comprising only a single electronic component secured to the sensor.

18. The system of claim 17, wherein the component is a capacitor and the capacitor is part of a parallel resonance circuit.

19. The system of claim 16, wherein the polymeric carrier includes a circular outer edge and a circular inner edge.

20. The system claim 16, wherein an eye-contacting surface of the polymeric carrier is parallel to an opposite outer surface of the polymeric carrier, and the polymeric carrier has a constant thickness along at least a majority of a length of the polymeric carrier.

21. The system of claim 16, further comprising a polymeric intermediate layer located between overlapping end portions of the passive inductor, the polymeric intermediate layer and the overlapping end portions being stacked in a direction perpendicular to an eye-contacting surface of the sensor.

22. The system of claim 21, wherein the overlapping end portions and the polymeric intermediate layer are a capacitor.

23. The system of claim 16, wherein the carrier comprises a concentric inner edge and a concentric outer edge with the passive inductor having undulating peaks being spaced away from but adjacent to the inner edge and the outer edge, and the inner edge and the outer edge being circular with an eye-contacting surface intersecting the inner edge and the outer edge.

24. The system of claim 23, further comprising a dissolvable polymeric film spanning across a central opening defined by the inner edge of the carrier.

25. An organ pressure sensing system comprising:
(a) an intraocular sensor including a metallic inductor within a polymeric carrier;
(b) the inductor including a wavy shape along a majority thereof with alternating peaks and valleys;
(c) the carrier being flexible and having a partially spherical, eye sclera-contacting surface;
(d) the inductor being a single loop of no greater than 360 degrees;
(e) the carrier including an outer segment between outermost of the peaks and an outer edge of the carrier, the peaks being spaced away from the outer edge;

(f) the carrier having an inner segment between innermost of the peaks and an inner edge, the innermost peaks being spaced away from the inner edge;

(g) an inductor lateral radial dimension defined between an inner circle, intersecting the innermost peaks, and an outer circle, intersecting the outermost peaks, being a majority of a carrier lateral radial dimension defined between the inner edge and the outer edge; and (h) a polymeric intermediate layer located between overlapping end portions of the inductor, the polymeric intermediate layer and the overlapping end portions being stacked in a direction perpendicular to the eye sclera-contacting surface.

26. The system of claim 25, wherein the overlapping end portions and the polymeric intermediate layer are a capacitor.

27. The system of claim 25, wherein the inner edge and the outer edge of the carrier are circular and concentric with each other.

28. The system of claim 25, further comprising:
a reader comprising a conductive coil, a microprocessor and a power supply;
the reader being spaced away from the sensor; and
the reader being configured to wirelessly communicate with the sensor using the inductor as an antenna.

29. The system of claim 25, wherein the sensor is free of a microprocessor or battery, and the inductor is a metallic variable inductor.

30. The system of claim 25, wherein the sensor is adapted for removable placement on a human eye, the carrier and sensor have an open center configured for placement coaxial with a pupil center point, and the sensor is configured to be removably and externally mounted to the eye without surgical implantation.

31. The system of claim 25, wherein a thickness of the carrier on each side of the inductor is 3-10 μm, and a thickness of the inductor is 500-900 nm, configured to allow stretching thereof based on intraocular pressure changes.

* * * * *